(12) United States Patent
Bellin et al.

(10) Patent No.: US 7,544,375 B1
(45) Date of Patent: Jun. 9, 2009

(54) COMPOSITION

(75) Inventors: Howard T. Bellin, New York, NY (US); Beatrice De Borg, West Hollywood, CA (US)

(73) Assignee: Swiss Skin Repair, Inc., Las Vegas, NV (US)

( * ) Notice: Subject to any disclaimer, the term of this patent is extended or adjusted under 35 U.S.C. 154(b) by 0 days.

(21) Appl. No.: 11/811,324

(22) Filed: Jun. 8, 2007

Related U.S. Application Data

(60) Provisional application No. 60/813,240, filed on Jun. 12, 2006.

(51) Int. Cl.
*A61K 36/00* (2006.01)

(52) U.S. Cl. ............... 424/725; 424/401; 514/2

(58) Field of Classification Search ............... None
See application file for complete search history.

(56) References Cited

U.S. PATENT DOCUMENTS

| | | | |
|---|---|---|---|
| 2,831,854 A | 4/1958 | Tucker et al. | |
| 3,963,699 A | 6/1976 | Rizzi et al. | |
| 4,005,195 A | 1/1977 | Jandacek | |
| 4,005,196 A | 1/1977 | Jandacek | |
| 4,517,360 A | 5/1985 | Volpenhein | |
| 4,518,772 A | 5/1985 | Volpenhein | |
| 4,797,300 A | 1/1989 | Jandacek et al. | |
| 4,976,953 A | 12/1990 | Orr et al. | |
| 4,985,459 A | 1/1991 | Sunshine et al. | |
| 5,306,514 A | 4/1994 | Letton et al. | |
| 5,306,515 A | 4/1994 | Letton et al. | |
| 5,306,516 A | 4/1994 | Letton et al. | |
| 5,498,420 A | 3/1996 | Mentrup et al. | |
| 5,910,306 A | 6/1999 | Alving et al. | |
| 6,338,855 B1 | 1/2002 | Albacarys et al. | |
| 6,471,972 B1 | 10/2002 | Bonte et al. | |
| 6,641,848 B1 | 11/2003 | Bonte et al. | |
| 6,846,812 B2 * | 1/2005 | Dalko et al. | ................ 514/171 |
| 6,866,856 B2 | 3/2005 | Lu et al. | |
| 6,891,063 B1 | 5/2005 | Mora et al. | |
| 6,974,799 B2 | 12/2005 | Lintner | |
| 7,022,317 B2 | 4/2006 | Erdelmeier et al. | |
| 7,029,660 B2 | 4/2006 | Goppel et al. | |
| 2005/0089500 A1 * | 4/2005 | Pinnell | ................ 424/74 |

OTHER PUBLICATIONS http://www.ageless.co.za/centella.htm—accessed Oct. 2008.*
http://www.studiodirectcosmetics.com/cosmetics/lip-plumper.htm—accessed Oct. 2008.*
Sederma, Darutoside, Product Information sheet, Aug. 4, 2004, Sederma, Edison, New Jersey, USA.
Sederma, Regestril, Product Information sheet, Mar. 7, 2006, Sederma, Edison, New Jersey, USA.
Sederma, Matrixyl, Product Information sheet, Feb. 10, 2006, Sederma, Edison, New Jersey, USA.
Bessler et al. "The Mitogenic Principle of *Escherichia coli* Lipoprotein: B-Lymphocyte Mitogenicity of the Synthetic Analouge Palmitoyl-Tetrapeptide", Biochemical and Biophysical Research Communications, May 31, 1984, 121:55, Academic Press, Inc., U.S.A.

* cited by examiner

*Primary Examiner*—Susan C Hoffman

(57) ABSTRACT

A topically applied composition or cream for treatment of the skin. A preferred composition includes a) a skin plumper; b) a tetrapeptide; c) a soya plant extract; d) Centella Asiatica extract; e) a cosmetic soothing or anti-inflammatory component; f) a component that acts on fibronectin synthesis; g) a moisturizing component; h) a structured conditioning component; i) an emulsifier component; and j) a transdermal delivery agent.

7 Claims, No Drawings

COMPOSITION

COMPOSITION

This application claims the benefit under 35 U.S.C. 119(e) of U.S. Provisional Patent Application No. 60/813,240 filed Jun. 12, 2006. Such provisional application is hereby incorporated by reference in its entirety into this application.

FIELD OF THE INVENTION

The present invention relates to a composition, particularly to a topically applied composition, and specifically to a topically applied composition for treatment of the skin and its underlying tissue for minimizing issues relating to stretch marks, fine lines and wrinkles.

BACKGROUND OF THE INVENTION

The present invention, instead of for injection into the skin, is for transdermal delivery via a topical application.

SUMMARY OF THE INVENTION

The present invention relates to a composition for treating, preventing, and improving the appearance of skin.

The present invention further relates to treating, preventing, ameliorating, reducing and/or eliminating stretch marks, fine lines and/or wrinkles of skin.

A preferred composition includes a) a skin plumper; b) a tetrapeptide; c) a soya plant extract, where components a, b and c are present at about 4 wt %; d) Centella Asiatica extract at about 2 wt %; e) a cosmetic soothing or anti-inflammatory component at about 2 wt %; f) a component that acts on fibronectin synthesis at about 3 wt %; g) a moisturizing component at about 2.5 wt %; h) a structured conditioning component at about 1 wt %; i) an emulsifier component at about 1 wt %; and j) a transdermal delivery agent at about 1.5 wt %.

DESCRIPTION

The present composition preferably includes a skin plumper (part A), a tetrapeptide (part B), a soya plant extract (part C), Centella Asiatica extract (part D), a cosmetic soothing or anti-inflammatory component (part E), a component that acts on fibronectin synthesis (part F), a moisturizing component (part G), a structured conditioning component (part H), an emulsifier component (part I), and a transdermal delivery agent (part J). Preferably, all parts are present in the final composition. However, if desired, one or more parts may be omitted. Further, one or more components of a part may be combined to make up such part.

Part A: A Skin Plumper

A skin plumper serves as a collagen enhancer to the skin. An example of a suitable and preferred skin plumper is palmitoyl oligopeptide (which may be identified by CAS number 171263-26-6 or 147732-56-7). Other nonlimiting examples of skin plumpers include collagen and/or glycosaminoglycan (GAG) enhancing agents. The skin plumper may be present from about 0.0001 wt % to about 40 wt %, preferably present from about 0.0001 wt % to about 20 wt %, more preferably from about 0.0001 wt % to about 10 wt %, even more preferably from about 0.0001 wt % to about 5.0 wt %, yet more preferably from about 0.0001 wt % to about 1.0 wt %, and most preferably from about 0.0001 wt % to about 0.10 wt % of the total weight of the composition.

Part B: Tetrapeptide or Tetrapeptides

The term "tetrapeptide" in accordance with the present invention is a compound that includes an uninterrupted sequence of four amino acids within its structure. These are indicated herein using a traditional three letter convention from left (N-terminal end) to right (C-terminal end). In this nomenclature, Gly is glycine, His is histidine, Lys is lysine, Pro is proline, Gln is glutamine and Arg is arginine.

The cosmetic compositions of the present invention preferably contain a safe and effective amount of at least one tetrapeptide. These may be one or more rigin-based tetrapeptides, one or more ALAMCAT-tetrapeptides or mixtures thereof. These tetrapeptides may be naturally occurring or of synthetic origin.

Rigin-based tetrapeptides in accordance with the present invention are based on the structure Gly-Gln-Pro-Arg and include its analogs and derivatives thereof.

Rigin is a preferred tetrapeptide. Analogs of the tetrapeptide rigin useful in accordance with the present invention include those in which one or more of the four amino acids are reorganized or rearranged within the sequence and/or where no more than two of the amino acids are substituted (e.g., Ala-Gln-Thr-Arg). More preferably, at least one of the amino acids within the sequence is Pro or Arg and most preferably the tetrapeptide includes both Pro and Arg although their order and position may vary. The amino acid substitutions can be from amongst any amino acid as defined herein. Particularly preferred rigin-based tetrapeptides include Xaa-Xbb-Arg-Xcc, Xaa-Xbb-Xcc-Pro, Xaa-Xbb-Pro-Arg, wherein Xaa-Xbb-Pro-Xcc, Xaa-Xbb-Xcc-Arg, Xaa, Xbb and Xcc may be the same or different and selected from the following Xaa is Gly or the amino acids that may be substituted therefore, Xbb is Gln or the amino acids that may be substituted therefore and Xcc may be Pro or Arg or the amino acids substituted therefore. The most preferable amino acids substituted for Gly include an aliphatic side chain such as, without limitation, beta-Ala, Ala, Val, Leu, Pro, Sarcosine (Sar) and Ile. The most preferable amino acids substituted for Gln include a side chain that includes an amine group that is predominantly uncharged at neutral pH (pH 6-7) such as, without limitation, Asn, Lys, Orn, 5-hydroxyproline, Citrulline and Canavanine. When Arg is substituted, it is preferably replaced with an amino acid having a side chain that includes, predominantly, a charged nitrogen at a pH of about 6, such as, without limitation, Pro, Lys, His, Desmosine and Isodesmosine.

Derivatives are also considered to be encompassed by the term rigin-base tetrapeptides in accordance with the present invention, (and therefore also the more generic term tetrapeptides). Derivatives include derivatives of the substituted and rearranged rigin-based tetrapeptides described herein. These derivatives include, inter alia, acyl-derivatives, which are tetrapeptides substituted with one or more straight-chain or branched-chain, long or short chain, saturated or unsaturated, substituted with a hydroxy, amino, amino acyl, sulfate or sulfide group or unsubstituted having from 1 to 29 carbon atoms. N-acyl-derivatives include those acyl groups which can be derived from acetic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid and the like. Preferable examples of the acyl group include an acetyl group, a palmitoyl group, an elaidoyl group, a myristyl group, a biotinyl group and an octanoyl group. These may be substituted or unsubstituted. When substituted, they are preferably substituted with hydroxyl or, sulphur containing groups such as, without limitation $SO_3H$, SH or S—S.

ALAMCAT tetrapeptides are tetrapeptides which include at least one amino acid including an aliphatic group containing side chain. These amino acids include, without limitation, Gly, beta-Ala, Ala, Val, Leu, Sarcosine (Sar) and Ile. These tetrapeptides also include at least one amino acid including at least one $NH_2$— containing side chain. These amino acids include a side chain that has an amine group that is predominantly uncharged at neutral pH (pH 6-7) such as, without limitation, Gln, Asn, Lys, Orn, 5-hydroxyproline, Citrulline and Canavanine. The ALAMCAT-tetrapeptides also include at least one amino acid having at least one side chain including at least one cationic amine (predominant species is charged such as $NH_3^+$, $NH_2^+$, etc.—basic amino acids which are positively charged at pH about 6.0). These amino acids include, without limitation, Pro, Arg, Lys, His, Desmosine and Isodesmosine. The remaining amino acid can be any amino acid, but is preferably one containing an alphatic group, pendant amino group or pendant cationic group.

Derivatives are also considered to be encompassed by the term ALAMCAT-tetrapeptides in accordance with the present invention, (and therefore also the more generic term tetrapeptides). These derivatives include, inter alia, acyl-derivatives, which are tetrapeptides substituted with one or more straight-chain or branched-chain, substituted or unsubstituted long or short chain, saturated or unsaturated acyl group(s) having from 1 to 29 carbon atoms. The acyl groups which can be used are the same as those described for the rigin-based tetrapeptides.

Preferred embodiments include N-acyl-Gly-Gln-Pro-Arg peptides, most preferably N-palmitoyl-Gly-Gln-Pro-Arg.

Preferred commercially available sources of tetrapeptides include RIGIN, EYELISS and MATRIXYL RELOADED, MATRIXYL 3000, which contain between 50 to 500 ppm of palmitoyl-Gly-Gln-Pro-Arg, and other ingredients, such as peptides, chalcones and an excipient, commercially available from SEDERMA, France. These may be used to produce compositions of the present invention by adding thereto at least one tripeptide as described herein.

The most preferred tetrapeptide of the present invention is palmitoyl tetrapeptide-3 (under INCI nomenclature where INCI stands for the International Nomenclature of Cosmetic Ingredients). Palmitoyl tetrapeptide-3 is a synthetic peptide that is a fragment of immunoglobulin G that has been combined with palmitic acid to make it more lipophillic and thus enhance its affinity towards human skin. Palmitoyl tetrapeptide-7 was formerly known as palmitoyl tetrapeptide-3.

The tetrapeptides of the present invention are preferably used in amounts from about 0.00001 wt % to about 5.0 wt %, more preferably from about 0.00001 wt % to about 1.0 wt %, even more preferably from about 0.00001 wt % to about 0.1 wt %, and yet more preferably from about 0.00001 wt % to about 0.01 wt % by weight of the composition.

Part C: Soya Plant Extract

The present composition includes at least one soya plant saponin extract or component, or at least one saponin or sapogenol extracted from a plant rich in such compounds. Such component can be extracted from a soya plant selected from the group consisting of *Glycine max* (soya), *Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotrys* and *Trifolium repens*, or a plant of the *Medicago* type, particularly *Medicago alfalfa* and *Medicago sativa*, or "alfalfa", as a cosmetic agent for increasing the amount of collagen IV in the dermo-epidermal junction.

The soya plant effective ingredient is preferably *Phaseolus lunatus* (where *Phaseolus lunatus* is the botanical name and where lima bean is the common name).

The soya plant effective ingredient can be part of a saponin or sapogenol or soya plant carrier. The soya plant extract is a concentration solution of the effective ingredient. Such saponin or sapogenol or soya plant extract is preferably between about 0.0001% and about 5.0% by weight, more preferably between about 0.0001 and about 2.0% by weight, yet more preferably between about 0.0001 and about 1.0% by weight, and most preferably between about 0.0001 and about 0.1% by weight based on the total weight of the final composition.

The effective ingredient in the soya plant extract, such as *Phaseolus lunatus*, is present in a dermatological or cosmetically effective amount, and such amount can be from about 0.1 μg/ml to about 1000 μg/ml, more preferably from about 1.0 μg/ml to about 100 μg/ml, relative to the saponin or sapogenol.

Part D: a Centella Asiatica Extract

The present composition includes a Centella Asiatica extract such as an acid or salt thereof and glycosylated derivatives thereof such as asiaticoside or madecassoside. The Centella Asiatica extract (in dry form or in a concentrated solution having the effective ingredient Centella Asiatica), can be present in an amount of from about 0.01 wt % to about 5.0 wt %, preferably about 0.01 wt % to about 2.0 wt %, more preferably from about 0.01 wt % to about 1.0 wt %, and most preferably from about 0.01 wt % to about 0.50 wt %, of the final composition. Centella Asiatica can have a modulating activity on connective tissue through an action on the fibroblasts and on two amino acids fundamental for the metabolism of the collagen: proline and alanine. Part D can be referred to as a connective tissue modulator.

Part E: Cosmetic Soothing or Anti-Inflammatory Component

Cosmetic soothing actives can be effective in preventing or treating inflammation of the skin. The soothing active enhances the skin appearance benefits of the present composition, e.g., such agents contribute to a more uniform and acceptable skin tone or color. The exact amount of anti-inflammatory agent to be used in the compositions will depend on the particular anti-inflammatory agent utilized since such agents vary widely in potency. Nonlimiting examples of cosmetic soothing agents include the following categories: propionic acid derivatives; acetic acid derivatives; fenamic acid derivatives; biphenylcarboxylic acid derivatives; and oxicams. All of these cosmetic soothing actives are fully described in U.S. Pat. No. 4,985,459 to Sunshine et al., issued Jan. 15, 1991, incorporated by reference herein in its entirety. Nonlimiting examples of useful cosmetic soothing actives include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, absinthium, acacia, aescin, alder buckthorn extract, allantoin, aloe, APT (available from Centerchem), arnica, *astragalus, astragalus* root extract, azulene, Baicalin SR 15 (available from Barnet Products Dist.), baikal skullcap, baizhu, balsam canada, bee pollen, BIOPHYTEX (available from Laboratories Serobiologiques), bisabolol, black cohosh, black cohosh extract blue cohosh, blue cohosh extract, boneset, borage, borage oil, bradykinin antagonists, bromelain, *calendula, calendula* extract, Canadian Willowbark Extract (available from Fytokem), candelilla wax, Cangzhu, canola phytosterols,

*capsicum*, carboxypeptidase, celery seed, celery stem extract, CENTAURIUM (available from Sederma), centaury extract, chamazulene, chamomile, chamomile extract, chaparral, chaste tree, chaste tree extract, chickweed, chicory root, chicory root extract, chirata, chishao, collodial oatmeal, comfrey, comfrey extract, CROMOIST CM GLUCAN (available from Croda), darutoside, dehurian angelica, devil's claw, divalent metals (such as, magnesium, strontium, and manganese), doggrass, dogwood, Eashave (available from Pentapharm), eleuthero, ELHIBIN (available from Pentapharm), ENTELINE 2 (available from Secma), ephedra, epimedium, esculoside; ethacrynic acid, evening primrose, eyebright, Extract LE-100 (available from Sino Lion), Fangfeng, feverfew, ficin, forsythia fruit, Fytosterol 85 (available from Fytokem), *ganoderma*, gaoben, Gatuline A (available from Gattefosse) gentian, germanium extract, gingko bilboa extract, ginkgo, ginseng extract, goldenseal, gorgonian extract, gotu kola, grape fruit extract, guaiac wood oil, guggal extract, helenalin esters, henna, honeysuckle flower, horehound extract, horsechestnut, horsetail, huzhang, *hypericum*, ichthyol, immortelle, ipecac, job's tears, jujube, kola extract, LANACHRYS 28 (available from Lana Tech), lemon oil, lianqiao, licorice root, ligusticum, *ligustrum*, lovage root, *luffa*, mace, magnolia flower, manjistha extract, margaspidin, matricin, melatonin, MICROAT IRC (available from Nurture), mints, mistletoe, Modulene (available from Seporga), mono or diglucosides of glabridin, mono or diglucosides of gentisin, MTA (5'-deoxy-5'-methylhioadenosine), mung bean extract, musk, N-methyl arginine, oat beta glucan, oat extract, orange, panthenol, papain, phenoxyacetic acid, peony bark, peony root, Phytoplenolin (available from Bio Botanica), phytosphingosine, Preregen (available from Pentapharm), purslane, QUENCH T (available from Centerchem), quillaia, red sage, rehmannia, rhubarb, rosemary, rosmarinic acid, royal jelly, rue, rutin, sandlewood, sanqi, sarsaparilla, saw palmetto, SENSILINE (available from Silab), SIEGESBECKIA (available from Sederma), stearyl glycyrrhetinate, Stimutex (available from Pentapharm), storax, strontium nitrate, sweet birch oil, sweet woodruff, tagetes, tea extract, thyme extract, tienchi ginseng, tocopherol, tocopheryl acetate, triclosan, turmeric, urimei, ursolic acid, white pine bark, witch hazel xinyi, yarrow, yeast extract, yucca, and mixtures thereof.

The preferred cosmetic soothing or anti-inflammatory component is darutoside. Another preferred cosmetic soothing or anti-inflammatory agent is rutin.

Such cosmetic soothing or anti-inflammatory component is preferably present in an amount of from about 0.001 wt % to about 5.0 wt %, more preferably from about 0.001 wt % to about 2.0 wt %, yet more preferably from about 0.001 wt % to about 1.0 wt %, and most preferably from about 0.001 wt % to about 0.10 wt % of the final composition.

Part F: Agents that Act on Fibronectin Synthesis

The present composition includes at least one active agent for stimulating dermal macromolecules or for preventing their degradation, especially those that act on fibronectin synthesis. Those agents that act on fibronectin synthesis include the extract of the zooplankton Salina sold by the company Seporga under the trade name GP4G; the yeast extract available especially from the company Alban Muller under the trade name Drieline; and the palmitoyl pentapeptide-4 sold by the company Sederma in a composition having the trade name Matrixil. Palmitoyl pentapeptide-4 is preferred.

Such agent is preferably present in an amount from about 0.0001 wt % to about 10.0 wt %, more preferably from about 0.0001 wt % to about 5.0 wt %, yet more preferably from about 0.0001 wt % to about 1.0 wt %, even yet more preferably from about 0.0001 wt % to about 0.1 wt %, and most preferably from about 0.0001 wt % to about 0.01 wt % of the final composition.

Part G: Moisturizing Component

The water phase or moisturizing component of the composition can include cosmetic auxiliaries, such as, for example, distilled, purified and/or deionised water, alcohols, in particular those of low carbon number, preferably ethanol or isopropanol, diols or polyols of low carbon number, and ethers thereof, preferably propylene glycol, glycerol (glycerin), butylene glycol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes, and in particular one or more thickeners, which may advantageously be chosen from the group consisting of silicon dioxide, aluminum silicates or polysaccharides or derivatives thereof, e.g. hyaluronic acid and/or its salt (such as sodium hyaluronate) or hyaluronan or hyaluronate, xanthan gum, hydroxypropylmethylcellulose, particularly advantageously from the group of polyacrylates, preferably a polyacrylate from the group of so-called Carbopols [from Bf. Goodrich], for example carbopol grades 980, 981, 1382, 2984, 5984, ETD 2020, ETD 2050, Ultrez 10, in each case individually or in combination. Another preferred thickener is carbomer or carboxypolymethylene. It should be noted that the term hyaluronate refers to the conjugate base of hyaluronic acid. Because such molecule typically exists in vivo in its polyanionic form, it is most commonly referred to as hyaluronan.

The water phase or moisturizing component may also be selected from the group comprising gly acrylic polymer (Lubragel), petrolatum, ethylhexyl palmitate, and hyaluronic acid sodium salt.

The compositions of the present invention may contain a moisturizing component selected from humectants or skin conditioners. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, glucosamine); hyaluronic acid; lactamide monoethanolamine; acetamide monoethanolamine; panthenol; allantoin; and mixtures thereof. Also useful herein are the propoxylated glycerols described in U.S. Pat. No. 4,976,953, to Orr et al., issued Dec. 11, 1990, which is hereby incorporated by reference in its entirety.

Also useful are various $C_1$-$C_{30}$ monoesters and polyesters of sugars and related materials. These esters are derived from a sugar or polyol moiety and one or more carboxylic acid moieties. Such ester materials are further described in U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; and U.S. Pat. No. 4,517,360, to Volpenhein, issued May 21, 1985, all of which are hereby incorporated by reference in their entireties.

The moisturizing agent may be selected from urea, guanidine, sucrose polyester, panthenol, dexpanthenol, allantoin, hyaluronic acid and combinations thereof. One preferred moisturizing agent is sodium hyaluronate.

The moisturizing component can include one or more emollients and one or more humectants. Emollients generally provide improved moisture retention in the skin and plasticization or softening of the skin. Humectants generally attract moisture, retard evaporation of water from the skin surface, and plasticize or soften skin. Emollients include mineral oil; petrolatum; aliphatic alcohols, such as stearyl alcohol; lanolin and its derivatives; glycol stearate; and fatty acids, such as triethanolamine oleate; and oils including alkyl (C12-15) benzoate or benzoic acid or C12-15 alkyl ester. Humectants include glycerin, propylene glycol, sorbitols, and polyethylene glycols.

Where the moisturizing component includes an emollient such as an oil, the oil or oil phase of the emulsions, oleogels or hydrodispersions or lipodispersions may be selected from the group of esters of saturated and/or unsaturated, branched and/or unbranched alkanecarboxylic acids with a chain length of from 3 to 30 carbon atoms and saturated and/or unsaturated, branched and/or unbranched alcohols with a chain length of from 3 to 30 carbon atoms, from the group of esters of aromatic carboxylic acids and saturated and/or unsaturated, branched and/or unbranched alcohols with a chain length of from 3 to 30 carbon atoms. Such ester oils can then be selected from the group consisting of isopropyl myristate, isopropyl palmitate, isopropyl stearate, isopropyl oleate, n-butyl stearate, diisopropyl adipate, n-hexyl laurate, n-decyl oleate, glyceryl stearate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of said esters, e.g. jojoba oil. In addition, the oil or oil phase can be selected from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can be selected from the group of synthetic, semisynthetic and natural oils, e.g. olive oil, sunflower oil, soybean oil, peanut oil, rapeseed oil, almond oil, palm oil, coconut oil, palm kernel oil and the like. The fatty acid can be tribehenin (glyceryl behenate or docosanoic acid). Mixtures of such oil and wax components may also be used. Waxes, such as cetyl palmitate, may be used as the lipid component of the oil phase. The oil or oil phase may be selected from the group consisting of 2-ethylhexyl isostearate, isohexadecane, octyldodecanol, isotridecyl isononanoate, isoeicosane, 2-ethylhexyl cocoate, $C_{12}$ $C_{15}$-alkyl benzoate, caprylic/capric acid triglyceride, dicaprylyl ether. Mixtures of $C_{12}$ $C_{15}$-alkyl benzoate and 2-ethylhexyl isostearate, mixtures of $C_{12}$ $C_{15}$-alkyl benzoate and isotridecyl isononanoate, and mixtures of $C_{12}$ $C_{15}$-alkyl benzoate, 2-ethylhexyl isostearate and isotridecyl isononanoate may be used. Of the hydrocarbons, paraffin oils, squalane and squalene may be used. Oil or oil components also include, for example, butyloctyl salicylate (for example that available under the trade name HALLBRITE BHB from CP Hall), hexadecyl benzoate and butyloctyl benzoate and mixtures thereof (Hallstar AB) and/or diethylhexyl naphthalate (Hallbrite TQ). The oil or oil phase can also include a content of cyclic or linear silicone oils. Cyclomethicone (octamethylcyclotetrasiloxane) may be used as a silicone oil to be used according to the invention. However, other silicone oils can also be used, for example hexamethylcyclotrisiloxane, polydimethylsiloxane, poly(methylphenylsiloxane). Mixtures of cyclomethicone and isotridecyl isononanoate, and of cyclomethicone and 2-ethylhexyl isostearate may be used.

The moisturizing component or components can be present at a level of from about 0.01% to about 70.0%, more preferably from about 0.01% to about 60%, and still more preferably from about 0.01% to about 50%, and most preferably from about 0.01% to about 45% by weight of the composition.

Where the moisturizing component is butylene glycol, this moisturizing component can be present at a level of from about 20.0% to about 70.0%, more preferably from about 25.0% to about 65.0%, even more preferably from about 30.0% to about 60.0%, still more preferably from about 35.0% to about 55.0%, and most preferably from about 40.0% to about 50% by weight of the composition.

Where the moisturizing component is water, this moisturizing component can be present at a level of from about 0.1% to about 25.0%, more preferably from about 0.1% to about 20.0%, even more preferably from about 0.1% to about 15.0%, and still more preferably from about 5.0% to about 15.0% by weight of the composition. The water is preferably distilled, purified and/or deionised.

Where the moisturizing component is glycerin, this moisturizing component can be present at a level of from about 1.0% to about 20.0%, more preferably from about 2.0% to about 18.0%, even more preferably from about 3.0% to about 15.0%, and still more preferably from about 4.0% to about 15.0%, and most preferably from about 5.0% to about 15.0% by weight of the composition.

Where the moisturizing component is a carbomer, this moisturizing component can be present at a level of from about 0.01% to about 2.0%, more preferably from about 0.01% to about 1.5%, and even more preferably from about 0.01% to about 1.0% by weight of the composition.

Where the moisturizing component is $C_{12-15}$ alkyl benzoate, this moisturizing component can be present at a level of from about 1.0% to about 30.0%, more preferably from about 1.0% to about 25.0%, even more preferably from about 1.0% to about 20.0%, and still more preferably from about 5.0% to about 20.0% by weight of the composition.

Where the moisturizing component is tribehenin, this moisturizing component can be present at a level of from about 0.01% to about 10.0%, more preferably from about 0.1% to about 10.0%, even more preferably from about 0.1% to about 10.0%, and still more preferably from about 1.0% to about 10.0% by weight of the composition.

Where the moisturizing component is sodium hyaluronate or a hyaluronan or a hyaluronan equivalent or derivative, this moisturizing component can be present at a level of from about 0.1% to about 30.0%, more preferably from about 0.1% to about 25.0%, even more preferably from about 0.1% to about 20.0%, and still more preferably from about 0.1% to about 15.0% by weight of the composition.

Part H: Structured Conditioning Component

The present composition includes a structured conditioning component. Preferred structured conditioning agents include vesicular structures such as ceramides and liposomes. Of these, ceramides are preferred. Of ceramides, ceramides-2 is preferred where ceramide 2 or ceramides-2 is INCI nomenclature.

Ceramides consist of a long-chain or sphingoid base linked to a fatty acid via an amide bond.

The structured conditioning component can be present at a level of from about 0.001% to about 5.0%, preferably from about 0.001% to about 4.0%, more preferably from about 0.001% to about 3.0%, and still more preferably from about 0.001% to about 2.0% by weight of the composition.

The structured conditioning component can be included within a coacervate-forming composition. Preferably, the coacervate-forming composition comprises a cationic polymer, an anionic surfactant, and a dermatologically acceptable carrier for the polymer and surfactant. The cationic polymer may be selected from the group consisting of natural backbone quaternary ammonium polymers, synthetic backbone quaternary ammonium polymers, natural backbone amphoteric type polymers, synthetic backbone amphoteric type polymers, and combinations thereof.

More preferably, the cationic polymer is selected from the group consisting of natural backbone quaternary ammonium polymers selected from the group consisting of Polyquaternium-4, Polyquaternium-10, Polyquaternium-24, PG-hydroxyethylcellulose alkyldimonium chlorides, guar hydroxypropyltrimonium chloride, hydroxypropylguar hydroxypropyltrimonium chloride, and combinations thereof; synthetic backbone quaternary ammonium polymers selected from the group consisting of Polyquaternium-2, Polyquaternium-6, Polyquaternium-7, Polyquaternium-11, Polyquaternium-16, Polyquaternium-17, Polyquaternium-18, Polyquaternium-28, Polyquaternium-32, Polyquaternium-37, Polyquaternium-43, Polyquaternium-44, Polyquaternium-46, polymethacylamidopropyl trimonium chloride, acrylamidopropyl trimonium chloride/acrylamide copolymer, and combinations thereof; natural backbone amphoteric type polymers selected from the group consisting of chitosan, quaternized proteins, hydrolyzed proteins, and combinations thereof; synthetic backbone amphoteric type polymers selected from the group consisting of Polyquaternium-22, Polyquaternium-39, Polyquaternium-47, adipic acid/dimethylaminohydroxypropyl diethylenetriamine copolymer, polyvinylpyrrolidone/dimethylyaminoethylmethacyrlate copolymer, vinylcaprolactam/polyvinylpyrrolidone/dimethylaminoethylmethacrylate copolymer, vinaylcaprolactam/polyvinylpyrrolidone/dimethylaminopropylmethacrylamide terpolymer, polyvinylpyrrolidone/dimethylaminopropylmethacrylamide copolymer, polyamine, and combinations thereof; and combinations thereof. Even more preferably, the cationic polymer is a synthetic backbone amphoteric type polymer. Even still more preferably, the cationic polymer is a polyamine.

When the cationic polymer is a polyamine, it is preferred that the cationic polyamine polymer be selected from the group consisting of polyethyleneimines, polyvinylamines, polypropyleneimines, polylysines and combinations thereof. Even more preferably, the cationic polyamine polymer is a polyethyleneimine.

In certain embodiments in which the cationic polymer is a polyamine, the polyamine may be hydrophobically or hydrophilically modified. In this instance, the cationic polyamine polymer is selected from the group consisting of benzylated polyamines, ethoxylated polyamines, propoxylated polyamines, alkylated polyamines, amidated polyamines, esterified polyamines and combinations thereof. The coacervate-forming composition comprises from about 0.01% to about 20%, more preferably from about 0.05% to about 10%, and most preferably from about 0.1% to about 5%, by weight of the coacervate-forming composition, of the cationic polymer.

Preferably, for the coacervate-forming composition, the anionic surfactant is selected from the group consisting of sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isethionates, glycerylether sulfonates, sulfosuccinates and combinations thereof. More preferably, the anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

Suitable coacervate-forming compositions are further described in copending U.S. patent application Ser. No. 09/397,747, filed in the name of Schwartz et al.; Ser. No. 09/397,746, filed in the name of Heinrich et al.; Ser. No. 09/397,712, filed in the name of Schwartz et al.; Ser. No. 09/397,723, filed in the name of Heinrich et al.; and Ser. No. 09/397,722, filed in the name of Venkitaraman et al.; each of which were filed on Sep. 16, 1999 and all of which are hereby incorporated by reference in their entireties.

Alternatively, the coacervate-forming composition may comprise an anionic polymer, a cationic surfactant, and a dermatologically acceptable carrier for the polymer and surfactant. The anionic polymer may be selected from the group consisting of polyacrylic acid polymers, polyacrylamide polymers, copolymers of acrylic acid, acrylamide, and other natural or synthetic polymers (e.g., polystyrene, polybutene, polyurethane, etc.), naturally derived gums, and combinations thereof. Suitable gums include alginates (e.g., propylene glycol alginate), pectins, chitosans (e.g., chitosan lactate), and modified gums (e.g., starch octenyl succinate), and combinations thereof. More preferably, the anionic polymer is selected from the group consisting of polyacrylic acid polymers, polyacrylamide polymers, pectins, chitosans, and combinations thereof. Preferred final compositions of the present invention comprise from about 0.01% to about 20%, more preferably from about 0.05% to about 10%, and most preferably from about 0.1% to about 5%, by weight of the coacervate-forming composition, of the anionic polymer. Suitable cationic surfactants include, but are not limited to, those discussed herein.

The structured conditioning component of the final composition is suitable for providing therapeutic or aesthetic skin benefits by deposition onto such surfaces of not only conditioning agents but also various agents including, but not limited to, anti-acne actives, anti-wrinkle actives, anti-microbial actives, anti-fungal actives, anti-inflammatory actives, topical anesthetic actives, artificial tanning agents and accelerators, anti-viral agents, enzymes, sunscreen actives, anti-oxidants, skin exfoliating agents, and combinations thereof.

Part I: Emulsifier Component

The emulsifier component or components is/are advantageously chosen from the group consisting of the following compounds: PEG-10 rapeseed sterol, polyglyceryl-2 dipolyhydroxystearate, PEG-30 dipolyhydroxystearate, cetyidimethicone copolyol, glycol distearate, glycol dilaurate, diethylene glycol dilaurate, sorbitan trioleate, glycol oleate, glyceryl dilaurate, sorbitan tristearate, propylene glycol stearate, propylene glycol laurate, propylene glycol distearate, sucrose distearate, PEG-3 castor oil, pentaerythrityl monostearate, pentaerythrityl sesquioleate, glyceryl oleate, glyceryl stearate, propylene glycol stearate, glyceryl diisostearate, pentaerythrityl monooleate, sorbitan sesquioleate, isostearyl diglyceryl succinate, glyceryl caprate, palm glycerides, glyceryl stearate, cholesterol, lanolin, lanolin alcohols, glyceryl oleate (containing 40% monoester), polyglyceryl-2 sesquiisostearate, polyglyceryl-2 sesquioleate, PEG-20 sorbitan beeswax, sorbitan oleate, sorbitan isostearate, trioleyl phosphate, glyceryl stearate and ceteareth-20 (Teginacid from Th. Goldschmidt), sorbitan stearate, sorbitan isostearate, PEG-7 hydrogenated castor oil, steareth-2, oleth-2, cetyl alcohol and ceteareth-30 (emulsifier E 2209 from Th. Goldschmidt), PEG-5 soya sterol, PEG-6 sorbitan beeswax, ceteth-2, glyceryl stearate SE, methylglucose sesquistearate, PEG-10 hydrogenated castor oil, sucrose distearate, oleth-3, sorbitan palmitate, PEG-22/dodecyl glycol copolymer, polyglyceryl-2 PEG-4 stearate, laneth-5, ceteth-3, laureth-3, ceteareth-3, stearyl alcohol and steareth-7 and steareth-10 (emulsifier E-2155 from Th. Goldschmidt), oleth-5, sorbitan laurate, laureth4, PEG-4 laurate, polysorbate 61, polysorbate 81, beheneth-10, polysorbate 65, polysorbate 80, laneth-10, triceteareth-4 phosphate, triceteareth-4 phosphate and sodium $C_{14-17}$-alkyl sec sulfonate (Hostacerin CG from Hoechst), PEG-8 stearate, glyceryl stearate and PEG-100 stearate (Arlacel 165 from ICI), polysorbate 85, trilaureth-4 phosphate, PEG-25 glyceryl trioleate, oleth-10, steareth-10, ceteth-10, PEG-35 castor oil, sucrose stearate, PEG-8 oleate, trioleth-8 phosphate, PEG-40 sorbitan lanolate, PEG-15 glyceryl ricinoleate, choleth-24 and ceteth-24 (Solulan C-24 from Amerchol), $C_{12-15}$-Pareth-12, PEG-20 glyceryl isostearate, polysorbate 60, PEG-40 hydrogenated castor oil, PEG-16 soya sterol, PEG-20 glyceryl oleate, PEG-20 stearate, polysorbate 80, PEG-20 methylglucose sesquistearate, PEG-30 glyceryl isostearate, PEG-20 glyceryl laurate, ceteth-20, ceteareth-25, PEG-30 stearate, PEG-30 glyceryl stearate, polysorbate 20, laureth-23, PEG-40 stearate, PEG-30 glyceryl laurate, PEG-50 stearate, PEG-100 stearate, PEG-150 laurate, polyglyceryl-3 methylglucose distearate, ceteareth-12, ceteareth-20 and steareth-21.

In addition, the emulsifier(s) is/are preferably chosen from the group of fatty acids which are completely or partially neutralized with customary alkalis (such as, for example, sodium and potassium hydroxide, sodium and potassium carbonate, and mono- and triethanolamine). Particularly advantageous are, for example, stearic acid and stearates, isostearic acid and isostearates, palmitic acid and palmitates, and also myristic acid and myristates.

It may be advantageous for the purposes of the present composition to choose the emulsifier(s) from the group of fatty alcohols which have a chain length of more than 8 carbon atoms. Particular preference may be given, for example, to cetyl, stearyl, myristyl and behenyl alcohol.

For the purposes of the present invention, it is advantageous to choose the emulsifier content (one or more components) from the range about 0.001% by weight to about 5.0% by weight, preferably about 0.001% by weight to about 2.0% by weight, and more preferably about 0.01% by weight to about 2.0% by weight.

Part J: Transdermal Delivery Agent

The transdermal delivery agent preferably includes a lipoaminoacid or lipopeptide component selected from the group consisting of collagen oleoyltetra- and pentapeptide, capryloyl collagen aminoacids, myristoyl hydrolyzed animal protein, dipalmitoyl hydroxy proline, and palmitoyl collagen aminoacids.

Liposomes of the present composition are closed vesicles surrounding an internal aqueous space. The internal compartment is separated from the external medium by a lipid bilayer composed of discrete lipid molecules. They may be composed of a variety of lipid components such as, for example, phospholipid, nonionic surfactant, synthetic or natural lipid, saturated or unsaturated lipid, and charged or neutral lipid, either with or without a sterol. Liposomes may be either multilamellar, paucilamellar, or unilamellar, and may be made in different sizes: small being less than 25 nm, intermediate being 25 nm to 500 nm, and large being greater than 500 nm. A typical liposome is composed of dimyristoyl phosphatidylcholine (DMPC), dimyristoyl phosphatidylglycerol (DMPG), and cholesterol, with or without lipid A, in a multilamellar configuration, and has a population of sizes from about 0.2 μm to about 10 μm. Parts A-I of the present composition may delivered by the delivery system of Part J of the present composition through intact skin to cells within the body, where an cosmetically favorable response is induced.

Liposomes of the present composition can be used as a transdermal delivery system of Parts A-I listed above.

Liposomes may be preformed and then mixed with Parts A-I. Liposomes may also be formed so as to contain Parts A-I inserted in the lipid bilayer, in the inner aqueous spaces, associated with the outer leaflet of the lipid bilayer, in the surrounding solution, or in any combination of these arrangements. Parts A-I may be dissolved or suspended, and then added to (a) the preformed liposomes in a lyophilized state, (b) dried lipids as a swelling solution or suspension, or (c) the solution of lipids used to form liposomes. The liposomes may either be used unwashed, or washed prior to use to remove antigen that is not associated with the liposome.

The liposomes may contain one or more of Parts A-I, or the liposomes containing separate parts of Parts A-I may be mixed into a single liposome formulation.

The present composition as a whole may be applied in the form of an emulsion, gel, solution, suspension, or other forms.

It is noted that hyaluronic acid or sodium hyaluronate is conventionally employed with compositions that are injected into the skin. Here it is believed that the transdermal delivery component of the present invention, including dipalmitoyl hydroxyproline, can be employed to transfer hyaluronic acid or sodium hyaluronate or hyaluronan or a hyaluronan equivalent or a hyaluronan derivative into the skin.

The transdermal delivery component can be present at a level of from about 0.1% to about 25.0%, more preferably from about 0.1% to about 20.0%, and still more preferably from about 0.1% to about 15.0% by weight of the composition.

The transdermal delivery takes place without perforation of the skin.

Other Components

Other components can include fillers or carriers or active or inert components such as water, lanolin, cocoa butter, shea butter, a fragrance, a preservative, perfume, or aloe.

Method of Making

Parts A-J may be mixed over time at room temperature such as for 1-4 hours, or may be mixed and heated such as at 40° C. to 80° C. for about 30 minutes to 3 hours, until well blended or thoroughly dispersed. The final composition may be in the form of a liquid, gel or cream.

All percentages and ratios used herein are by weight of the total composition.

The pH of the composition when in liquid, gel or cream form may be between about 5.7 and about 6.7, is preferably between about 5.8 and 6.6, and is most preferably between about 6.2 and 6.4.

Parts A-J may be placed in an industrial high speed blender. Parts A-J may be homogenized.

Method of Application

The present composition, when in cream form, is applied topically to a localized area. The composition is applied by hand and rubbed into the skin. The composition is applied daily once or twice. The composition can be applied on a daily basis (once or twice per day) for an unlimited period of time.

If not applied on a daily basis, the composition can be applied every other day or at another interval, such as every third day or every fourth day, for an unlimited amount of time. If applied once or twice every day, the skin may show beneficial results in about two weeks, where such beneficial results may be the amelioration or at least partial disappearance of stretch marks, scarring, fine lines, and wrinkles.

The present composition can be incorporated into a pad or other holder and then rubbed over the skin. Or the composition can be present in cream form or liquid form or gel form and hand applied into the skin or applied to a pad or other absorbent holder that is then applied to the skin.

The present composition can be applied after warming the skin, such as with an electrical heating pad or a hot water heating pad. Application of the composition upon warm skin can enhance absorption.

INCORPORATION BY REFERENCE

As to the present composition, the following U.S. patents are hereby incorporated by reference herein in their entireties: 1) the Lintner U.S. Pat. No. 6,974,799 B2 issued Dec. 13, 2005 and entitled Compositions Containing Mixtures Of Tetrapeptides And Tripeptides; 2) the Lu et al. U.S. Pat. No. 6,866,856 issued Mar. 15, 2005 and entitled Compositions And Delivery Methods For The Treatment Of Wrinkles, Fine Lines And Hyperhidrosis; 3) the Bonte et al. U.S. Pat. No. 6,641,848 B1 issued Nov. 4, 2003 and entitled Saponin Or Sapogenol Compositions For Increasing Collagen IV Synthesis; 4) the Mora et al. U.S. Pat. No. 6,891,063 B3 issued May 10, 2005 and entitled Salts Of Asiatic And Madecassic Acid Suitable For The Preparation Of Pharmaceutical And Cosmetic Compositions; 5) the Bonte et al. U.S. Pat. No. 6,471,972 B1 issued Oct. 29, 2002 and entitled Cosmetic Treatment Method For Fighting Against Skin Ageing Effects; 6) the Albacarys et al. U.S. Pat. No. 6,338,855 issued Jan. 15, 2002 and entitled Cleansing Articles For Skin And/Or Hair Which Also Deposit Skin Care Actives; 7) the Erdelmeier et al. U.S. Pat. No. 7,022,317 issued on Apr. 4, 2006 and entitled Heterocyclic Derivatives Of 2-Oxothiazolidine-4-Carboxylic Acid, And Use As Active Photoprotective Agents; 8) the Goppel et al. U.S. Pat. No. 7,029,660 issued Apr. 18, 2006 and entitled Cosmetic Or Dermatological Light-Protective Formulation Comprising A Benzotriazole And A Benzoxazole Derivative; 9) the Mentrup et al. U.S. Pat. No. 5,498,420 issued Mar. 12, 1996 and entitled Stable Small Particle Liposome Preparations, Their Production And Use In Topical Cosmetic, And Pharmaceutical Compositions; and 10) the Alving et al. U.S. Pat. No. 5,910,306 issued Jun. 8, 1999 and entitled Transdermal Delivery System For Antigen.

As to the present composition, the following reference is hereby incorporated in reference in its entirety: 1) Bessler et al. "The Mitogenic Principle of *Escherichia coli* Lipoprotein: B-Lymphocyte Mitogenicity of the Synthetic Analouge Palmitoyl-Tetrapeptide", Biochemical and Biophysical Research Communications 121:55 (1984).

Composition A

Composition A is the preferred composition and is set out below. Methods for preparing Composition A are set out in Examples 1 and 2.

| Composition A | | | |
|---|---|---|---|
| Class | Compound | parts by weight | % by weight |
| Skin plumper (Part A) | palmitoyl oligopeptide | 0.13 | 0.008 |
| Tetrapeptide (Part B) | palmitoyl tetrapeptide-7 | 0.08 | 0.005 |
| Soya plant extract (Part C) | *Phaseolus lunatus* (green bean) extract | 0.016 | 0.001 |
| *Centella Asiatica* Extract (Part D) | *Centella Asiatica* extract | 3.6 | 0.21 |
| Cosmetic soothing or anti-inflammatory component (Part E) | rutin | 1.0 | 0.06 |
| Cosmetic soothing or anti-inflammatory component (Part E) | darutoside | 0.4 | 0.02 |
| Agents that act on fibronectin synthesis (Part F) | palmitoyl pentapeptide-4 (also known as palmitoyl pentapeptide-3) | 0.03 | 0.002 |
| Moisturizing component (Part G) | butylene glycol | 777.2 | 44.41 |
| Moisturizing component (Part G) or filler | water | 151.0 | 8.63 |
| Moisturizing component (Part G) | glycerin | 160.47 | 9.17 |
| Moisturizing component (Part G) or thickener | carbomer | 3.0 | 0.17 |
| Moisturizing component (Part G) or emollient | $C_{12-15}$ alkyl benzoate | 184.95 | 10.57 |
| Moisturizing component (Part G) or emollient | tribehenin | 50.0 | 2.86 |
| Moisturizing component (Part G) or thickener | sodium hyaluronate | 250 | 14.28 |
| Structured conditioning component (Part H) | cetyl hydroxy-ethylcellulose | 1.6 | 0.09 |
| Structured conditioning component (Part H) | ceramide 2 | 8.75 | 0.5 |
| Emulsifier (Part I) | PEG-10 rapeseed sterol | 6.25 | 0.36 |
| Emulsifier (Part I) | polysorbate 20 | 1.5 | 0.086 |
| Transdermal delivery agent (Part J) | dipalmitoyl hydroxy-proline | 150 | 8.57 |
| Total parts by weight | | 1750 | |
| Total % by weight (approximate) | | | 100 |

Preferred Ranges for the Components of Composition A
The preferred ranges for the components of Composition A are set out below.

| Composition A | | | |
|---|---|---|---|
| Class | Compound | Preferred range (% by weight) | Targeted % by weight |
| Skin plumper (Part A) | palmitoyl oligopeptide | 0.0001-0.10 | 0.008 |
| Tetrapeptide (Part B) | palmitoyl tetrapeptide-7 | 0.00001-0.10 | 0.005 |
| Soya plant extract (Part C) | Phaseolus lunatus (green bean) extract | 0.0001-0.10 | 0.001 |
| *Centella Asiatica* Extract (Part D) | *Centella Asiatica* extract | 0.01-2.0 | 0.21 |
| Cosmetic soothing or anti-inflammatory component (Part E) | rutin | 0.001-1.0 | 0.06 |
| Cosmetic soothing or anti-inflammatory component (Part E) | darutoside | 0.001-1.0 | 0.02 |

-continued

Composition A

| Class | Compound | Preferred range (% by weight) | Targeted % by weight |
|---|---|---|---|
| Agents that act on fibronectin synthesis (Part F) | palmitoyl pentapeptide-4 (also known as palmitoyl pentapeptide-3) | 0.0001–0.01 | 0.002 |
| Moisturizing component (Part G) | butylene glycol | 20.0–70.0 | 44.41 |
| Moisturizing component (Part G) or filler | water | 0.1–25.0 | 8.63 |
| Moisturizing component (Part G) | glycerin | 1.0–20.0 | 9.17 |
| Moisturizing component (Part G) or thickener | carbomer | 0.01–2.0 | 0.17 |
| Moisturizing component (Part G) or emollient | $C_{12-15}$ alkyl benzoate | 1.0–25.0 | 10.57 |
| Moisturizing component (Part G) or emollient | tribehenin | 0.01–10.0 | 2.86 |
| Moisturizing component (Part G) or thickener | sodium hyaluronate | 0.1–30.0 | 14.28 |
| Structured conditioning component (Part H) | cetyl hydroxyethylcellulose | 0.001–5.0 | 0.09 |
| Structured conditioning component (Part H) | ceramide 2 | 0.001–5.0 | 0.5 |
| Emulsifier (Part I) | PEG-10 rapeseed sterol | 0.001–5.0 | 0.36 |
| Emulsifier (Part I) | polysorbate 20 | 0.001–5.0 | 0.086 |
| Transdermal delivery agent (Part J) | Dipalmitoyl hydroxyproline | 0.1–25.0 | 8.57 |

Composition B

Composition B is another composition according to the present invention and is set out below. Methods for preparing Composition B are set out in Examples 3 and 4.

| Class | Component | Parts by weight | % by weight |
|---|---|---|---|
| Skin plumper (Part A) | palmitoyl oligopeptide | 1.83 | 1.83 |
| Tetrapeptide (Part B) | palmitoyl tetrapeptide-7 (Also known as palmitoyl tetrapeptide-3) | 1.82 | 1.82 |
| Soya plant extract (Part C) | *Phaseolus lunatus* (green bean) extract | 0.36 | 0.36 |
| *Centella Asiatica* Extract (Part D) | *Centella Asiatica* extract | 3.6 | 3.6 |
| Cosmetic soothing or anti-inflammatory component (Part E) | darutoside | 0.4 | 0.4 |
| Agents that act on fibronectin synthesis (Part F) | palmitoyl pentapeptide-4 (also known as palmitoyl pentapeptide-3) | 3.0 | 3.0 |
| Moisturizing component (Part G) | butylene glycol | 65.0 | 65.0 |
| Moisturizing component (Part G) | water | 17.5 | 17.5 |
| Moisturizing component (Part G) or thickener | Sodium hyaluronate | 2.5 | 2.5 |
| Structured conditioning component (Part H) | ceramide 2 | 1.45 | 1.45 |
| Emulsifier (Part I) | PEG-10 rapeseed sterol | 1.04 | 1.04 |
| Transdermal delivery agent (Part J) | dipalmitoyl hydroxyproline | 1.5 | 1.5 |
| Total parts by weight | | 100 | |
| % by weight | | | 100 |

Preferred Ranges for the Components of Composition B

The preferred ranges for the components of Composition B are set out below.

Composition B

| Class | Component | Preferred range (% by weight) | Targeted % by weight |
|---|---|---|---|
| Skin plumper (Part A) | palmitoyl oligopeptide | 0.0001–5.0 | 1.83 |
| Tetrapeptide (Part B) | palmitoyl tetrapeptide-7 | 0.00001–5.0 | 1.82 |
| Soya plant extract (Part C) | *Phaseolus lunatus* (green bean) extract | 0.0001–2.0 | 0.36 |
| *Centella Asiatica* Extract (Part D) | *Centella Asiatica* extract | 0.01–5.0 | 3.6 |
| Cosmetic soothing or anti-inflammatory component (Part E) | darutoside | 0.001–2.0 | 0.4 |
| Agents that act on fibronectin synthesis (Part F) | palmitoyl pentapeptide-4 (also known as palmitoyl pentapeptide-3) | 0.0001–5.0 | 3.0 |
| Moisturizing component (Part G) | butylene glycol | 20.0–70.0 | 65.0 |
| Moisturizing component (Part G) | water | 0.1–25.0 | 17.5 |
| Moisturizing component (Part G) or thickener | Sodium hyaluronate | 0.1–30.0 | 2.5 |
| Structured conditioning component (Part H) | ceramide 2 | 0.001–5.0 | 1.45 |
| Emulsifier (Part I) | PEG-10 rapeseed sterol | 0.001–5.0 | 1.04 |
| Transdermal delivery agent (Part J) | dipalmitoyl hydroxyproline | 0.1–25.0 | 1.5 |

EXAMPLE 1

Sub-composition 1 or sub-part 1 is provided. Sub-composition 1 consists essentially of the components of Table 1 set out below. Sub-composition 1 is available from Sederma of Edison, N.J. under the trade name REGESTRIL™.

TABLE 1

Sub-composition 1 or sub-part 1

| Class | Component | % by weight | CAS # |
|---|---|---|---|
| Moisturizing component (Part G) | butylene glycol | 80.3 | 107-88-0 |
| Moisturizing component (Part G) or filler | Water | 19 | 7732-18-5 |
| Structured conditioning component (Part H) | cetyl hydroxy-ethylcellulose | 0.4 | 80455-45-4 |
| Cosmetic soothing or anti-inflammatory component (Part E) | rutin | 0.25 | 153-18-4 |
| Skin plumper (Part A) | palmitoyl oligopeptide | 0.02 | 147732-56-7 |
| Tetrapeptide (Part B) | palmitoyl tetrapeptide-7 (Also known as palmitoyl tetrapeptide-3) | 0.02 | 221227-05-0 |
| Soya plant extract (Part C) | Phaseolus lunatus (green bean) extract | 0.004 | 85085-22-9 |
| Total % by weight | | about 100 | |

Sub-composition 2 or sub-part 2 is provided. Sub-composition 2 consists essentially of the components of Table 2 set out below. Sub-composition 2 is available from Sederma of Edison, N.J. under the trade name DARUTOSIDE™.

TABLE 2

Subcomposition 2 or sub-part 2

| Class | Component | % by weight | CAS # |
|---|---|---|---|
| Moisturizing component (Part G) | butylene glycol | 99.0 | 107-88-0 |
| Centella Asiatica Extract (Part D) | Centella Asiatica extract | 0.9 | 84696-21-9 |
| Cosmetic soothing or anti-inflammatory component (Part E) | darutoside | 0.1 | 59219-65-7 |
| Total % by weight | | about 100 | |

Sub-composition 3 or sub-part 3 is provided. Sub-composition 3 consists essentially of the components of Table 3 set out below. Sub-composition 3 is available from Sederma of Edison, N.J. under the trade name MATRIXYL™.

TABLE 3

Sub-composition 3 or sub-part 3

| Class | Component | % by weight | CAS # |
|---|---|---|---|
| Moisturizing component (Part C) | glycerin | 53.49 | 56-81-5 |
| Moisturizing component (Part G) | butylene glycol | 20.0 | 107-88-0 |
| Moisturizing component (Part G) or filler | water | 25 | 7732-18-5 |
| Moisturizing component (Part G) or thickener | carbomer | 1.0 | 9007-20-9 |
| Emulsifier (Part I) | polysorbate 20 | 0.5 | 9005-64-5 |
| Agents that act on fibronectin synthesis (Part F) | palmitoyl pentapeptide-4 (also known as palmitoyl pentapeptide-3) | 0.01 | 214047-004 |
| Total % by weight | | about 100 | |

Sub-composition 4 or sub-part 4 is provided. Sub-composition 4 consists essentially of the components of Table 4 set out below. Sub-composition 4 is available from Sederma of Edison, N.J. under the trade name DERMAXYL™.

TABLE 4

Sub-composition 4 or sub-part 4

| Class | Component | % by weight | CAS # |
|---|---|---|---|
| Moisturizing component (Part G) or emollient | $C_{12-15}$ alkyl benzoate | 73.98 | 68411-27-8 |
| Moisturizing component (Part G) or emollient | tribehenin | 20 | 18641-57-1 |
| Structured conditioning component (Part H) | ceramide 2 | 3.5 | 100403-19-8 |
| Emulsifier (Part I) | PEG-10 rapeseed sterol | 2.5 | 68441-03-2 |
| Skin plumper (Part A) | palmitoyl oligopeptide | 0.02 | 171263-26-6 |
| Total % by weight | | about 100 | |

Sub-part 5 is provided. Sub-part 5 consists essentially of the component of Table 5 set out below.

TABLE 5

Sub-part 5

| Class | Component | % by weight | CAS # |
|---|---|---|---|
| Moisturizing component (Part G) or thickener | Sodium hyaluronate | About 100 | 9067-32-7 |

Sub-part 6 is provided. Sub-part 6 consists essentially of the component of Table 6 set out below.

TABLE 6

| Sub-part 6 | | | |
|---|---|---|---|
| Class | Component | % by weight | CAS # |
| Transdermal delivery agent (Part J) | dipalmitoyl hydroxyproline | About 100 | 41672-81-5 |

Then, sub-parts 1-6 are mixed in the following ratios or parts by weight according to Table 7 below.

TABLE 7

| Composition A | | |
|---|---|---|
| Sub-part | Parts by weight | % by weight |
| 1 | 4.0 | 22.84 |
| 2 | 4.0 | 22.84 |
| 3 | 3.0 | 17.13 |
| 4 | 2.5 | 14.28 |
| 5 | 2.5 | 14.28 |
| 6 | 1.5 | 8.57 |
| Total subparts by weight | 17.5 | |
| Total % by weight | | about 100 |

Sub-parts 1-6 are to be mixed at room temperature for three hours or until well blended or the components are thoroughly dispersed.

EXAMPLE 2

Example 1 is repeated, except that sub-parts 1-6 are to be mixed at 40° C. for one hour or until well blended or the components are thoroughly dispersed.

EXAMPLE 3

The components as shown in Table 8 are to be mixed at room temperature for three hours or until well blended or the components are thoroughly dispersed.

TABLE 8

| Composition B | | | |
|---|---|---|---|
| Class | Component | Parts by weight | % by weight |
| Skin plumper (Part A) | palmitoyl oligopeptide | 1.83 | 1.83 |
| Tetrapeptide (Part B) | palmitoyl tetrapeptide-7 (Also known as palmitoyl tetrapeptide-3) | 1.82 | 1.82 |
| Soya plant extract (Part C) | Phaseolus lunatus (green bean) extract | 0.36 | 0.36 |
| *Centella Asiatica* Extract | *Centella Asiatica* extract | 3.6 | 3.6 |

TABLE 8-continued

| Composition B | | | |
|---|---|---|---|
| Class | Component | Parts by weight | % by weight |
| (Part D) Cosmetic soothing or anti-inflammatory component (Part E) | darutoside | 0.4 | 0.4 |
| Agents that act on fibronectin synthesis (Part F) | palmitoyl pentapeptide-4 (also known as palmitoyl pentapeptide-3) | 3.0 | 3.0 |
| Moisturizing component (Part G) | butylene glycol | 65.0 | 65.0 |
| Moisturizing component (Part G) | water | 17.5 | 17.5 |
| Moisturizing component (Part G) or thickener | Sodium hyaluronate | 2.5 | 2.5 |
| Structured conditioning component (Part H) | ceramide 2 | 1.45 | 1.45 |
| Emulsifier (Part I) | PEG-10 rapeseed sterol | 1.04 | 1.04 |
| Transdermal delivery agent (Part J) | dipalmitoyl hydroxyproline | 1.5 | 1.5 |
| Total parts by weight | | 100 | |
| % by weight | | | 100 |

EXAMPLE 4

Example 3 is repeated, except that the components of Table 8 are to be mixed at 40° C. for one hour or until well blended or the components are thoroughly dispersed.

EXAMPLE 5

Composition C is the result of Example 5.

Prior to mixing with the other sub-parts, sub-part 1 is adjusted so that, upon combination with the other sub-parts, palmitoyl oligopeptide (first portion), palmitoyl tetrapeptide-3, and *Phaseolus* lunatus (green bean) extract make up 4.0% by weight of composition C, with each of the three adjusted components being about 1.33% by weight of Composition C. The concentrations or % by weight of the remaining components of sub-part 1 are to be increased or reduced in proportion to such adjustment.

Prior to mixing with the other sub-parts, sub-part 2 is adjusted so that, upon combination with the other sub-parts, Centella Asiatica extract and darutoside make up 4.0% by weight of composition C, with each of the two adjusted components being about 2.0% by weight of Composition C. The concentrations or % by weight of the remaining components of sub-part 2 are to be increased or reduced in proportion to such adjustment.

Prior to mixing with the other sub-parts, sub-part 3 is adjusted so that, upon combination with the other sub-parts, palmitoyl pentapeptide-4 makes up 3.0% by weight of composition C. The concentrations or % by weight of the remaining components of sub-part 3 are to be increased or reduced in proportion to such adjustment.

Prior to mixing with the other sub-parts, sub-part 4 is adjusted so that, upon combination with the other sub-parts, ceramide 2, PEG-10 rapeseed sterol, and palmitoyl oligopeptide (second portion) make up 2.5% by weight of composition C, with each of the three adjusted components being about 0.833% by weight of Composition C. The concentrations or % by weight of the remaining components of sub-part 4 are to be increased or reduced in proportion to such adjustment.

Prior to mixing with the other sub-parts, sub-part 5 is adjusted so that, upon combination with the other sub-parts, sodium hyaluronate makes up 2.5% by weight of composition C.

Prior to mixing with the other sub-parts, sub-part 6 is adjusted so that, upon combination with the other sub-parts, dipalmitoyl hydroxyproline makes up 1.5% by weight of composition C.

Sub-parts 1-6 after adjustment are to be mixed, in equal amounts by weight, at room temperature for three hours or until well blended or the components are thoroughly dispersed.

EXAMPLE 6

Example 5 is repeated, except that sub-parts 1-6 after adjustment are to be mixed at 40° C. for one hour or until well blended or the components are thoroughly dispersed.

EXAMPLE 7

Composition D is the result of Example 7.
Sub-parts 1-6 of Example 1 are mixed in the following ratios or parts by weight according to Table 9 below.

TABLE 9

| Pre-composition D | | |
|---|---|---|
| Sub-part | Parts by weight | % by weight |
| 1 | 1.0 | 16.67 |
| 2 | 1.0 | 16.67 |
| 3 | 1.0 | 16.67 |
| 4 | 1.0 | 16.67 |
| 5 | 1.0 | 16.67 |
| 6 | 1.0 | 16.67 |
| Total sub-parts by weight | 6.0 | |
| Total % by weight | | about 100 |

Then, the concentrations of the components of pre-composition D are adjusted (such as by addition) such that palmitoyl oligopeptide (first portion), palmitoyl tetrapeptide-3, and *Phaseolus* lunatus (green bean) extract make up 4.0% by weight of final Composition D, with each of the three adjusted components being about 1.33% by weight of final Composition D, such that Centella Asiatica extract and darutoside make up 4.0% by weight of final Composition D, with each of the two adjusted components being about 2.0% by weight of final Composition D, such that palmitoyl pentapeptide-4 makes up 3.0% by weight of final Composition D, such that ceramide 2, PEG-10 rapeseed sterol, and palmitoyl oligopeptide (second portion) make up 2.5% by weight of final Composition D, with each of the three adjusted components being about 0.833% by weight of final Composition D, such that sodium hyaluronate makes up 2.5% by weight of final Composition D, and such that dipalmitoyl hydroxyproline makes up 1.5% by weight of final Composition D.

After adjustment, Composition D is to be mixed at room temperature for three hours or until well blended or the components are thoroughly dispersed.

EXAMPLE 8

Example 7 is repeated, except that Composition D, after adjustment, is to be mixed at 40° C. for one hour or until well blended or the components are thoroughly dispersed.

EXAMPLE 9

Sub-parts 1-6 of Example 1 are mixed in the following ratios or parts by weight according to Table 10 below.

TABLE 10

| Composition E | | |
|---|---|---|
| Sub-part | Parts by weight | % by weight |
| 1 | 100 | 24.0 |
| 2 | 100 | 24.0 |
| 3 | 100 | 24.0 |
| 4 | 100 | 24.0 |
| 5 | 10.4 | 2.5 |
| 6 | 6.3 | 1.5 |
| Total sub-parts by weight | 416.7 | |
| Total % by weight | | about 100 |

Sub-parts 1-6 are to be mixed at room temperature for three hours or until well blended or the components are thoroughly dispersed.

In detail, Composition E is shown in Table 11 below.

TABLE 11

| | Composition E | | |
|---|---|---|---|
| Class | Compound | parts by weight | % by weight |
| Skin plumper (Part A) | palmitoyl oligopeptide | 0.01 | 0.01 |
| Tetrapeptide (Part B) | palmitoyl tetrapeptide-7 | 0.005 | 0.005 |
| Soya plant extract (Part C) | *Phaseolus lunatus* (green bean) extract | 0.001 | 0.001 |
| *Centella Asiatica* Extract (Part D) | *Centella Asiatica* extract | 0.216 | 0.216 |
| Cosmetic soothing or anti-inflammatory component (Part E) | rutin | 0.06 | 0.06 |
| Cosmetic soothing or anti-inflammatory component (Part E) | darutoside | 0.024 | 0.024 |
| Agents that act on fibronectin synthesis (Part F) | palmitoyl pentapeptide-4 (also known as palmitoyl pentapeptide-3) | 0.0024 | 0.0024 |
| Moisturizing component (Part G) | butylene glycol | 47.83 | 47.83 |
| Moisturizing component (Part G) or filler | water | 10.56 | 10.56 |
| Moisturizing component (Part G) | glycerin | 12.84 | 12.84 |
| Moisturizing component (Part G) or thickener | carbomer | 0.24 | 0.24 |
| Moisturizing component (Part G) or emollient | $C_{12-15}$ alkyl benzoate | 17.75 | 17.75 |
| Moisturizing component (Part G) or emollient | tribehenin | 4.8 | 4.8 |

TABLE 11-continued

Composition E

| Class | Compound | parts by weight | % by weight |
|---|---|---|---|
| Moisturizing component (Part G) or thickener | sodium hyaluronate | 2.5 | 2.5 |
| Structured conditioning component (Part H) | cetyl hydroxy-ethylcellulose | 0.096 | 0.096 |
| Structured conditioning component (Part H) | ceramide 2 | 0.84 | 0.84 |
| Emulsifier (Part I) | PEG-10 rapeseed sterol | 0.4 | 0.4 |
| Emulsifier (Part I) | polysorbate 20 | 0.12 | 0.12 |
| Transdermal delivery agent (Part J) | dipalmitoyl hydroxyproline | 1.5 | 1.5 |
| Total parts by weight | | 99.7944 | |
| Total % by weight (approximate) | | | 100 |

EXAMPLE 10

Example 9 is repeated, except that sub-parts 1-6 are to be mixed at 40° C. for one hour or until well blended or the components are thoroughly dispersed.

EXAMPLE 11

The components as shown in Table 12 are to be mixed at room temperature for three hours or until well blended or the components are thoroughly dispersed.

TABLE 12

Composition F

| Class | Component | Parts by weight | % by weight |
|---|---|---|---|
| Skin plumper (Part A) | palmitoyl oligopeptide | 1.83 | 1.83 |
| Tetrapeptide (Part B) | palmitoyl tetrapeptide-7 (Also known as palmitoyl tetrapeptide-3) | 1.82 | 1.82 |
| Soya plant extract (Part C) | *Phaseolus lunatus* (green bean) extract | 0.36 | 0.36 |
| *Centella Asiatica* Extract (Part D) | *Centella Asiatica* extract | 3.6 | 3.6 |
| Cosmetic soothing or anti-inflammatory component (Part E) | darutoside | 0.4 | 0.4 |
| Agents that act on fibronectin synthesis (Part F) | palmitoyl pentapeptide-4 (also known as palmitoyl pentapeptide-3) | 3.0 | 3.0 |
| Moisturizing component (Part G) or thickener | Sodium hyaluronate | 2.5 | 2.5 |
| Structured conditioning component (Part H) | ceramide 2 | 1.45 | 1.45 |
| Emulsifier (Part I) | PEG-10 rapeseed sterol | 1.04 | 1.04 |
| Transdermal delivery agent | dipalmitoyl hydroxyproline | 1.5 | 1.5 |

TABLE 12-continued

Composition F

| Class | Component | Parts by weight | % by weight |
|---|---|---|---|
| (Part J) Components remaining from sub-parts 1-6 | Components remaining from sub-parts 1-6 | 82.5 | 82.5 |
| Total parts by weight | | 100 | |
| % by weight | | | 100 |

As to the components remaining from sub-parts 1-6, these are the components not shown in Table 12, but found in sub-parts 1-6. These remaining components are to be added in proportion to that shown in sub-parts 1-6 with the total weight of the remaining components being 82.5% by weight of Composition F.

EXAMPLE 12

Example 11 is repeated, except that the components of Table 11 are to be mixed at 40° C. for one hour or until well blended or the components are thoroughly dispersed.

Cosmetically Applicable Uses

The present composition provides an effective composition for treating, preventing, ameliorating, reducing and/or eliminating stretch marks, fine lines and/or wrinkles of skin. The present composition is intended to be applied to stretch marks, fine lines in the skin, and wrinkles. Further, the composition is intended to be applied to scars or to skin tissue that has scarred. Scars include stretch marks or stretch mark scars, burn scars, scars from a skin injury such as a scar from a cut, acne scars, and a chicken pox mark or chicken pox scar. It is believed that a stretch mark is a scar. It is believed that a chicken pox mark is a scar. It should be noted that a stretch mark can occur not only from child birth, but also from losing weight. Moreover, stretch marks can also occur in heretofore unknown ways and appear "out of the blue" with no known cause.

The present composition is a collagen builder and facial and body rejuvenator.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

We claim:

1. A composition comprising:
    a) palmitoyl oligopeptide in a range from about 0.0001% to about 0.10% by weight of the composition;
    b) palmitoyl tetrapeptide-7 in a range from about 0.00001% to about 0.10% by weight of the composition;
    c) *Phaseolus lunatus* (green bean) extract in a range from about 0.0001% to about 0.10% by weight of the composition;
    d) a Centella Asiatica component selected from the group of a Centella Asiatica extract, an acid of a Centella Asiatica extract, a salt of a Centella Asiatica extract, asiaticoside, madecassoside, and a concentrated solution of a Centella Asiatica extract, wherein said Centella Asiatica component is in a range from about 0.01% to about 2.0% by weight of the composition;
e) rutin in a range from about 0.001% to about 1.0% by weight of the composition;
f) darutoside in a range from about 0.001% to about 1.0% by weight of the composition;
g) palmitoyl pentapeptide-4 in a range from about 0.0001% to about 0.01% by weight of the composition;
h) butylene glycol in a range from about 20.0% to about 70.0% by weight of the composition;
i) water in a range from about 0.1% to about 25.0% by weight of the composition;
j) glycerin in a range from about 1.0% to about 20.0% by weight of the composition;
k) carbomer in a range from about 0.01% to about 2.0% by weight of the composition;
l) $C_{12-15}$ alkyl benzoate in a range from about 1.0% to about 25.0% by weight of the composition;
m) tribehenin in a range from about 0.01% to about 10.0% by weight of the composition;
n) sodium hyaluronate in a range from about 0.1% to about 30.0% by weight of the composition;
o) cetyl hydroxy-ethylcellulose in a range from about 0.001% to about 5.0% by weight of the composition;
p) ceramide 2 in a range from about 0.001% to about 5.0% by weight of the composition;
q) PEG-10 rapeseed sterol in a range from about 0.001% to about 5.0% by weight of the composition;
r) polysorbate 20 in a range from about 0.001% to about 5.0% by weight of the composition; and
s) dipalmitoyl hydroxyproline in a range from about 0.1% to about 25.0% by weight of the composition.

2. The composition of claim 1 wherein said Centella Asiatica component is a Centella Asiatica extract.

3. The composition of claim 1 wherein said Centella Asiatica component is an acid of a Centella Asiatica extract.

4. The composition of claim 1 wherein said Centella Asiatica component is a salt of a Centella Asiatica extract.

5. The composition of claim 1 wherein said Centella Asiatica component is asiaticoside.

6. The composition of claim 1 wherein said Centella Asiatica component is madecassoside.

7. The composition of claim 1 wherein said Centella Asiatica component is a concentrated solution of a Centella Asiatica extract.

* * * * *